United States Patent [19]
Bonutti et al.

[11] Patent Number: 5,320,611
[45] Date of Patent: Jun. 14, 1994

[54] EXPANDABLE CANNULA HAVING LONGITUDINAL WIRE AND METHOD OF USE

[75] Inventors: Peter M. Bonutti, 1303 W. Evergreen Pl., Effingham, Ill. 62401; James S. Hawkins, Urbana, Ill.

[73] Assignee: Peter M. Bonutti, Effingham, Ill.

[21] Appl. No.: 13,942

[22] Filed: Feb. 4, 1993

[51] Int. Cl.$^5$ .................. A61M 25/00; A61M 5/00
[52] U.S. Cl. .................................. 604/264; 604/280
[58] Field of Search ............ 604/164, 264, 280, 282; 128/898

[56] References Cited

U.S. PATENT DOCUMENTS

| | | |
|---|---|---|
| 3,788,318 | 1/1974 | Kim et al. |
| 3,789,852 | 2/1974 | Kim et al. |
| 3,811,449 | 5/1974 | Gravelee et al. |
| 4,461,281 | 7/1984 | Carson |
| 4,504,268 | 3/1985 | Herlitze et al. ............... 604/280 |
| 4,589,868 | 5/1986 | Dretler ............................ 604/96 |
| 4,630,609 | 12/1986 | Chin |
| 4,706,670 | 11/1987 | Andersen et al. ............... 604/282 |
| 4,716,901 | 1/1988 | Jackson et al. ............... 604/106 |
| 4,846,812 | 7/1989 | Walker et al. ............... 604/280 |
| 4,899,729 | 2/1990 | Gill et al. ...................... 606/198 |
| 4,954,126 | 9/1990 | Wallsten ........................ 600/36 |
| 4,996,583 | 10/1990 | Delsanti ........................ 606/198 |
| 4,998,539 | 3/1991 | Delsanti ........................ 128/898 |
| 5,037,404 | 8/1991 | Gold et al. .................... 604/280 |
| 5,069,674 | 12/1991 | Fearnot et al. ............... 604/280 |

*Primary Examiner*—Jerome L. Kruter
*Attorney, Agent, or Firm*—Tarolli, Sundheim & Covell

[57] ABSTRACT

Cannulas for surgical and medical use expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

46 Claims, 8 Drawing Sheets

Fig.20  Fig.21

EXPANDABLE CANNULA HAVING LONGITUDINAL WIRE AND METHOD OF USE

BACKGROUND OF THE INVENTION

The present invention relates to cannulas for surgical and medical use. A typical cannula is a fixed diameter tube which a surgeon uses to maintain an instrument passage through tissue to a subcutaneous working location. The surgeon must first make an incision the full depth of the cannula in order to insert the cannula. This traumatic action damages good tissue in order to get to bad tissue. It would be desirable to provide cannulas which do not require a full depth incision, or at least require only a needle-size entrance opening, and which still allow use of a cannula to maintain an instrument passage.

SUMMARY OF THE INVENTION

In accordance with the invention, cannulas are provided which expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF PREFERRED EMBODIMENTS

In a first embodiment of the invention, a cannula 10 (FIG. 1) includes an expanding portion 12 and a proximal end portion 14. The expanding portion 12 includes a plurality of longitudinally extending wires 16. The wires 16 are surrounded for most of their length by an overlying elastic sheath 18. The wires 16 define between them a central instrument passage 20.

Figures 1, 2:
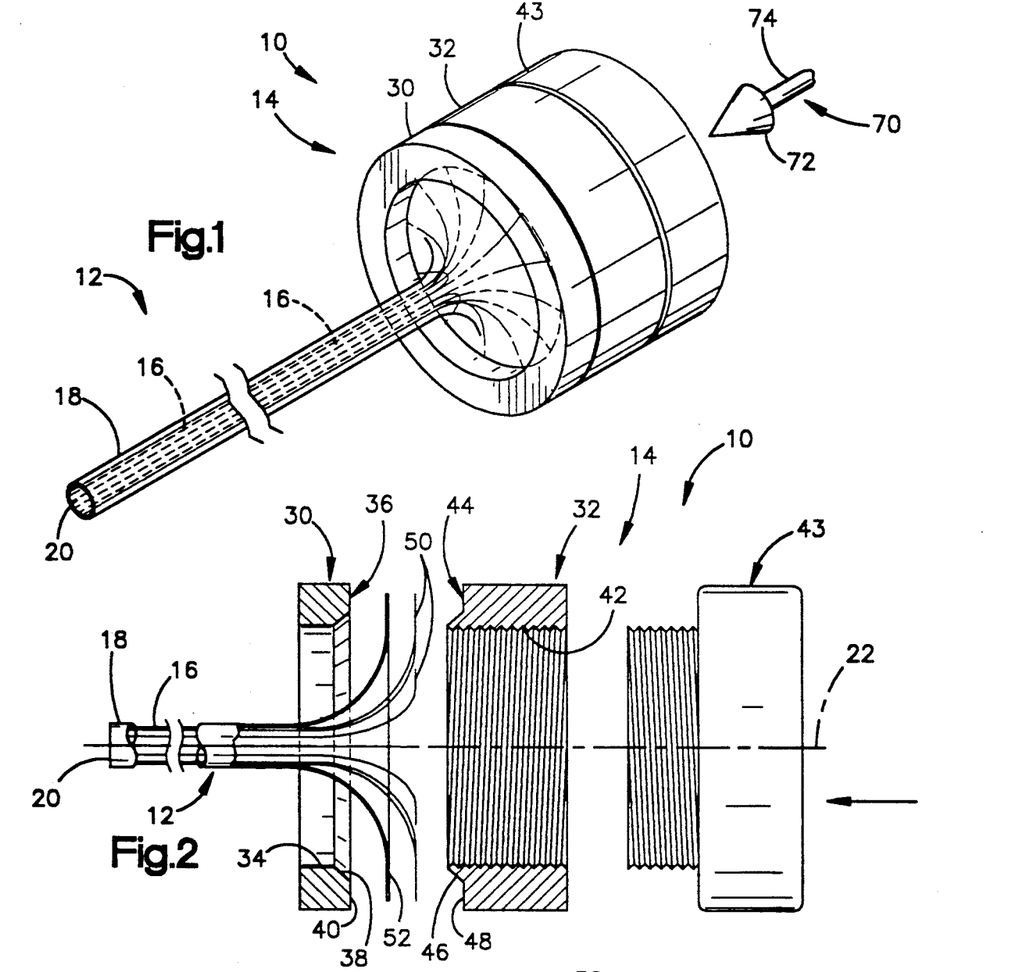
FIG. 1 is a perspective view of a cannula in accordance with a first embodiment of the invention, shown in an unexpanded condition.
FIG. 2 is an exploded longitudinal sectional view of the cannula of FIG. 1.

The wires 16 are preferably made of a material which is flexible. A preferred material is music wire, which is thin gauge steel about 0.015" in diameter. The use of the term "wire" in this application and its claims does not limit the invention to metal wires. The "wires" may also be made of other elongate material such as composites or plastics or other metals. The "wires" may also be coated.

The number of wires may be selected as desired. Applicants have found that 8 to 10 wires will suffice for a cannula expandable up to 7 mm OD, and that 12 wires or more may be necessary for a larger cannula. Ten larger diameter wires (0.025") may be used rather a larger number of small diameter wires. A greater number of wires 16 can be used if a greater diameter is needed. If not enough wires 16 are used, an instrument (trocar, insert, scope, etc.) inserted through the passage 20 when the cannula 10 is expanded will contact the elastic sheath 18 rather than the wires 16, at locations between the wires.

The wires 16 are self-aligning. When the cannula 10 is in a contracted condition, the wires 16 may overlap. When the cannula 10 is expanded, the wires 16 straighten out as shown.

The elastic sheath 18 is preferably secured to the wires 16 at both proximal and distal ends, to prevent the sheath's sliding off the wires during insertion and removal of the cannula 10. Rubber cement or cyanoacrylate or a similar adhesive can be used to bond the sheath 18 to the wires 16 as shown schematically at 24.

The elastic sheath 18 is preferably made of latex or silicone, or of C-Flex ®, a general purpose thermoplastic elastomer sold by Linvatec Corporation of Clearwater, Fla. The sheath 18 is of a diameter such that it is stressed even when the cannula 10 is fully contracted. Thus, the sheath 18 constantly biases the wires 16 radially inwardly toward the axis 22 of the cannula 10.

At the proximal end portion 14 of the cannula 10, the wires 16 are clamped between an inner ring member 30 and an outer ring member 32. The inner ring member 30 has a central opening 34. The inner ring member 30 has a clamping surface 36 including a beveled edge 38 and an annular radially extending surface 40. The outer ring member 32 has a threaded central opening 42 for receiving a standard luer lock 43. The outer ring member 32 has a clamping surface 44 including a beveled edge 46 and an annular radially extending surface 48.

The ring members 30 and 32 can be made of metal, in which case they can be brazed or welded together. The ring members 30 and 32 can be made of plastic, in which case then they can be UV joined or joined by adhesive.

Figure 3:
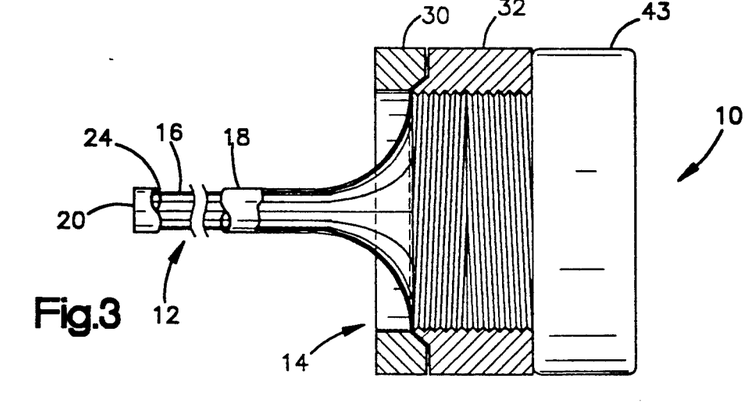
FIG. 3 is an assembled view of the cannula of FIG. 1.
Figure 4:
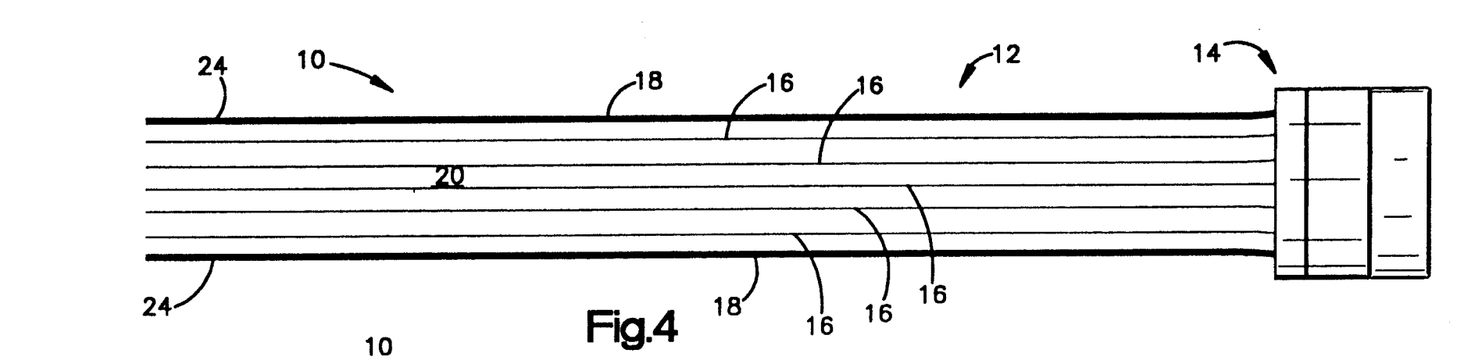
FIG. 4 is a schematic side view illustrating the cannula of FIG. 1 in an expanded condition.
Figure 5:
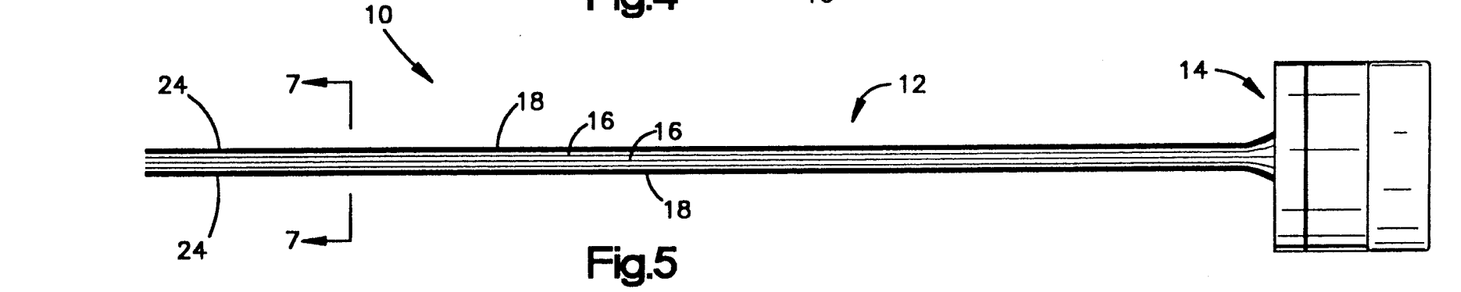
FIG. 5 is a schematic side view illustrating the cannula of FIG. 1 in a contracted or collapsed condition.

Proximal end portions 50 of the wires 16 are trapped between the ring members 30 and 32. When the ring members 30 and 32 are joined together as in FIG. 3, the proximal end portions 50 of the wires 16 are trapped between the clamping surface 36 of the inner ring 30 and the clamping surface 44 of the outer ring 32. The proximal end portion 52 of the sheath 18 is preferably also trapped between the rings 30 and 32, to secure the sheath proximally. Alternatively, the proximal end portion 52 of the sheath 18 may be bonded to the wires 16 at a proximal location adjacent the ring members 30 and 32. Thus, the proximal end of the cannula expanding portion 12 is secured, having a large diameter generally equal to the expanded diameter of the cannula 10.

The sheath 18 has a circumferential outer surface 54 (FIG. 7) and a circumferential inner surface 56. The wires 16 engage the circumferential inner surface 56 of the sheath 18. The radially inner surfaces 60 of the wires 16 define an annular periphery 62 within which any item inserted in the cannula 10 is disposed. In one embodiment which has been constructed, when contracted, the cannula 10 is about 2 mm diameter, the size of a 14 ga needle. Thus, the cannula 10 can possibly be inserted as a needle, clearing its own path, and not needing a trocar first. The constructed cannula is about 90 mm long. Other useful sizes include (i) up to 2.5 mm diameter with a 70 mm length; (ii) up to 7 mm diameter with a 110 mm length; and (iii) up to 11 mm diameter with a 160 mm length.

In use of the cannula 10, the surgeon makes a small incision in the epidermis. He inserts a narrow trocar such as the trocar 70 (FIGS. 6 and 8) into the central passage 20 of the cannula 10. The pointed end portion 72 of the trocar 70 will project distally. The shaft portion 74 of the trocar 70 is disposed inside the passage 20. The outer surface 76 of the trocar shaft portion 74 engage the radially inner surfaces 60 of the wires 16. The proximal end portion 78 of the trocar 70 extends proximally from the cannula 10.

Figure 6:
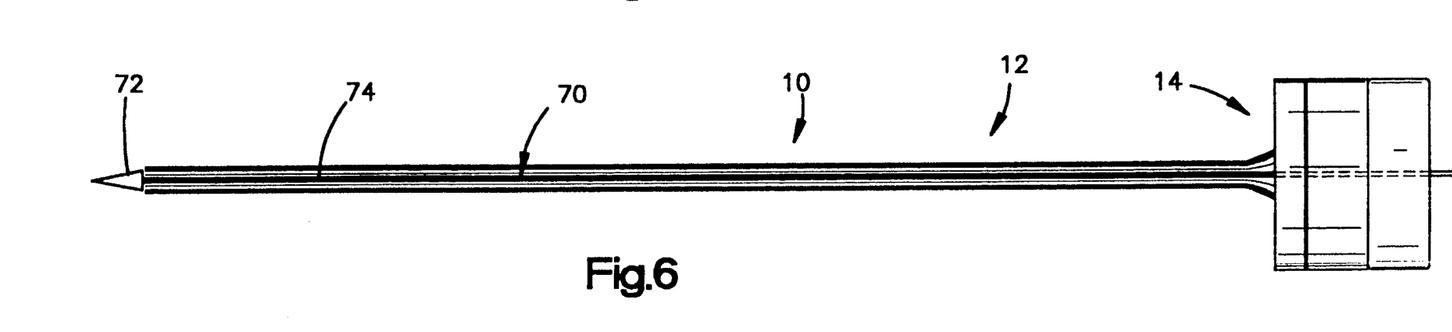
FIG. 6 is a side view similar to FIG. 5 illustrating a trocar inserted in the cannula of FIG. 1.

The end portion 72 of the trocar 70 may be blunt in order to push away internal tissue. In this case, a small incision would need to be made through the epidermis.

The trocar/cannula assembly is inserted through the incision in the epidermis to the subcutaneous working location. Then, a tubular insert 80 (FIG. 8) is moved distally between the wires 16 of the cannula 10 and the trocar 70. The insert 80 is preferably a hollow metal tube at least as large in ID as the OD of the trocar pointed end portion 72. The trocar 70 can then be removed from the cannula 10, leaving the cannula and the insert 80 in place in the tissue.

Figure 7:
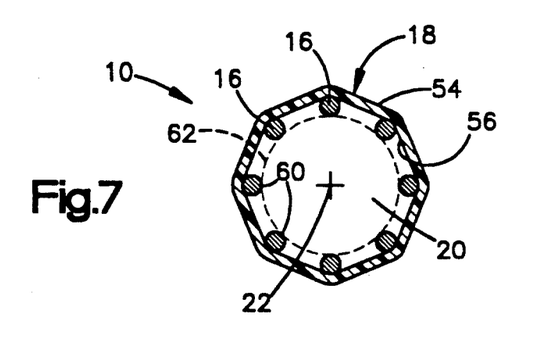
FIG. 7 is a sectional view taken along line 7—7 of FIG. 5.
Figure 8:
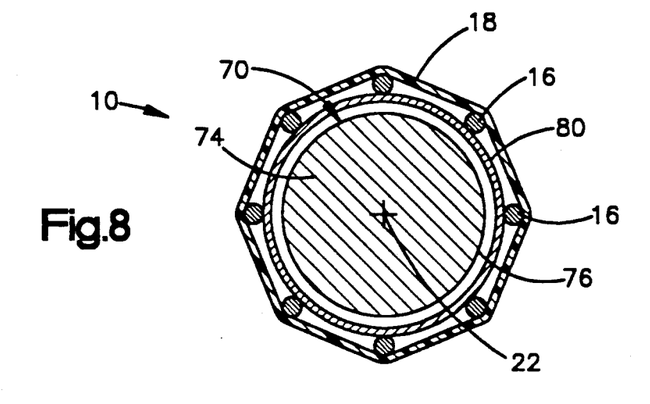
FIG. 8 illustrates the cannula of FIG. 7 in a partially expanded condition with a trocar and a tubular insert therein.

Because the insert 80 is larger in diameter than the trocar 70, during insertion of the insert 80, the cannula 10 is expanded radially outwardly, as seen in a comparison of FIGS. 7 and 8 (which are not necessarily to scale). The tissue around the cannula 10 is also stretched. The surgeon has thus made a larger passage for instruments, along its entire length, without cutting tissue.

After the tissue is allowed to relax, the surgeon removes the insert 80. The cannula 10 collapses radially inwardly because of the elastic sheath and because of the force of the tissue around it. But the tissue opening does not necessarily collapse completely, because of the viscoelastic nature of tissue, which tends to maintain its stretched condition for some time.

The surgeon then puts a second insert inside the cannula 10. The second insert is a hollow tube larger in diameter than the first insert 80. Again, the cannula expands radially outwardly, and the tissue stretches.

In this manner, the surgeon continues with larger and larger inserts, until the tissue opening is as large as desired. The cannula may then be in the expanded condition shown in FIG. 9, with a full size metal insert 90 within the cannula 80. The insert 90 then functions as a normal cannula, allowing insertion and removal of surgical instruments and the like.

Figure 12:
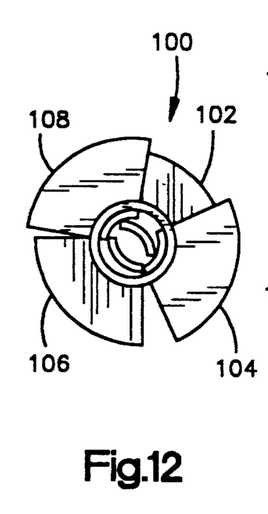
FIG. 12 is an end view of the cannula of FIG. 11 in a fully collapsed condition.

Items inserted through the central passage 20 of the cannula 10 always contact the inner cylindrical surface 92 of the insert 90. This provides a non-wearing, slippery engagement, which is desirable for insertion and removal of the instruments. An example is illustrated in FIG. 12 showing a probe 94 extending through the central instrument passage 20 of the cannula 10 having an insert 90 therein. The cannula 10 has expanded tissue 96 radially outwardly to create a cavity 98 therein.

Figure 9:
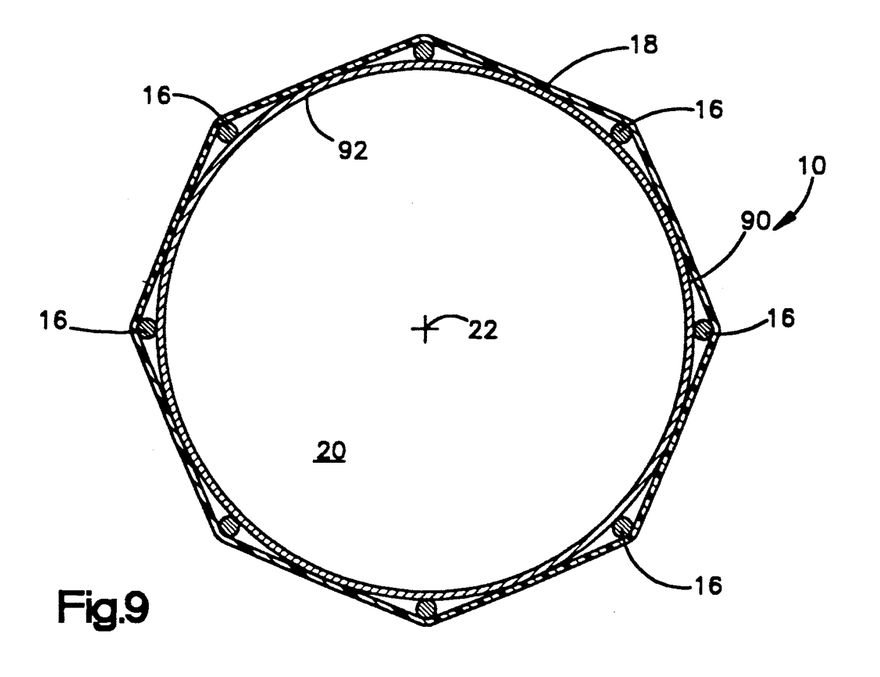
FIG. 9 illustrates the cannula of FIG. 7 in a fully expanded condition with a larger tubular insert therein.
Figure 10:
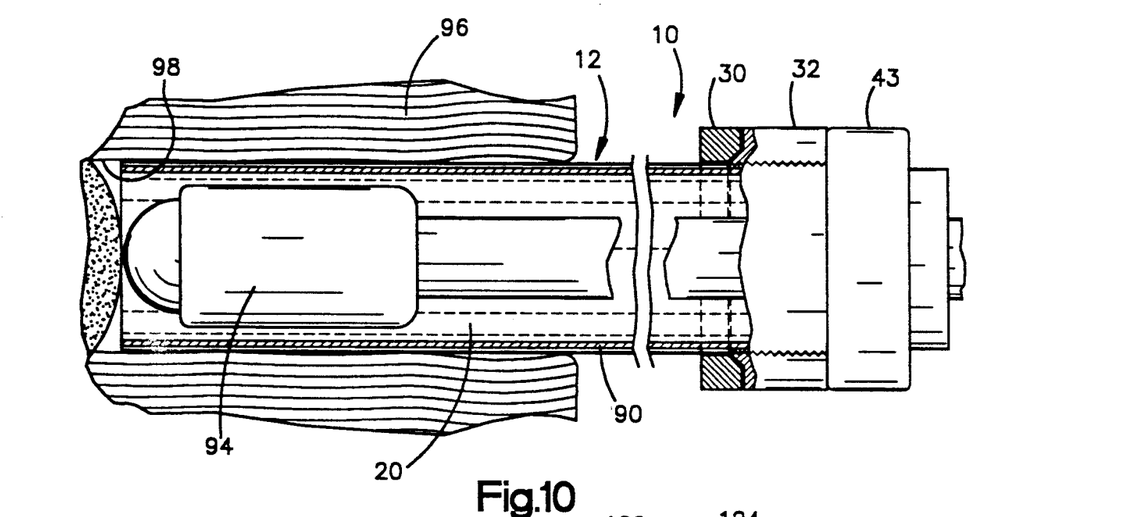
FIG. 10 illustrates the cannula of FIG. 1 in use.

Items inserted through the central passage 20 of the cannula 10, such as the inserts 80 and 90, always contact the radially inner surfaces 60 of the wires 16. This also provides a non-wearing, slippery engagement, which is desirable for insertion and removal of the inserts.

The cannula 10 is discarded after use to prevent contamination.

Thus, it is seen that the wires 16 have outer surface portions 60 disposed radially inwardly in the cannula 10 and forming contact surfaces for surgical instruments and the like inserted through the central instrument passage 20 of the cannula. The sheath 18 has an outer circumferential surface 54 engaging tissue when the cannula 10 is in use. The wires 16 block engagement of instruments inserted through the central instrument passage 20 of the cannula 16 with the elastic sheath 18. The sheath 18 blocks engagement of tissue with the wires 16, and the sheath and the wires block engagement of tissue with any instruments inserted through the cannula 10.

The cannula 10 expands radially outwardly along substantially its entire length against the bias of the sheath 18. Thus, the cannula 10 can accommodate through its central instrument passage 20 a surgical instrument or the like having a diameter along its entire length which is greater than the diameter of the cannula in the contracted condition. This is not possible with cannulas which expand only along a portion of their length.

A second embodiment of the invention is illustrated in FIGS. 11-17. An expandable cannula 100 includes four longitudinally extending members 102, 104, 106, and 108. Each member includes a longitudinally extending arcuate segment and a widened proximal end portion. The members 102, 104, 106, and 108 are made of plastic. One suitable material is Delrin ® brand plastic.

Figure 11:
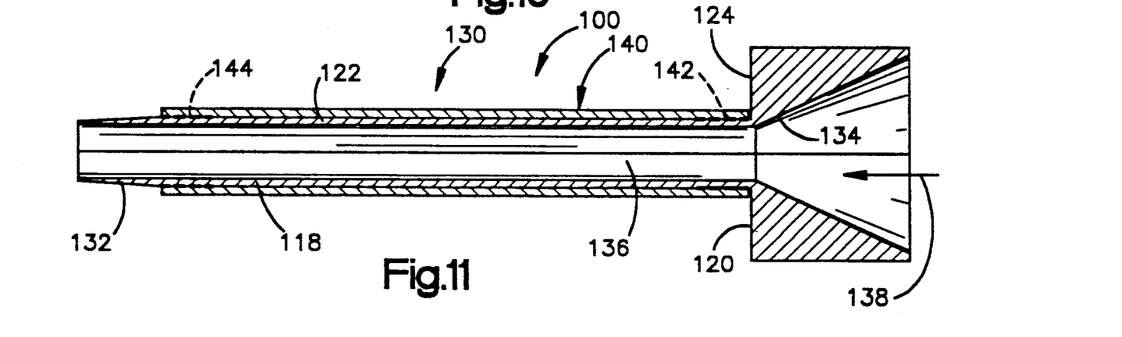
FIG. 11 is a view of a cannula in accordance with a second embodiment of the present invention, shown in an unexpanded condition.

Specifically, the member 102 includes a longitudinally extending arcuate segment 110 and a widened proximal end portion 112. The member 104 includes a longitudinally extending arcuate segment 114 and a widened proximal end portion 116. The member 106 includes a longitudinally extending arcuate segment 118 and a widened proximal end portion 120. The member 108 includes a longitudinally extending arcuate segment 122 and a widened proximal end portion 124.

The members 102, 104, 106, and 108 each subtend an angle of 90°. When the members 102, 104, 106, and 108 are placed together, their longitudinally extending arcuate segments 110, 114, 118, and 122 form a tubular expandable cannula structure 130.

Figures 15, 16:
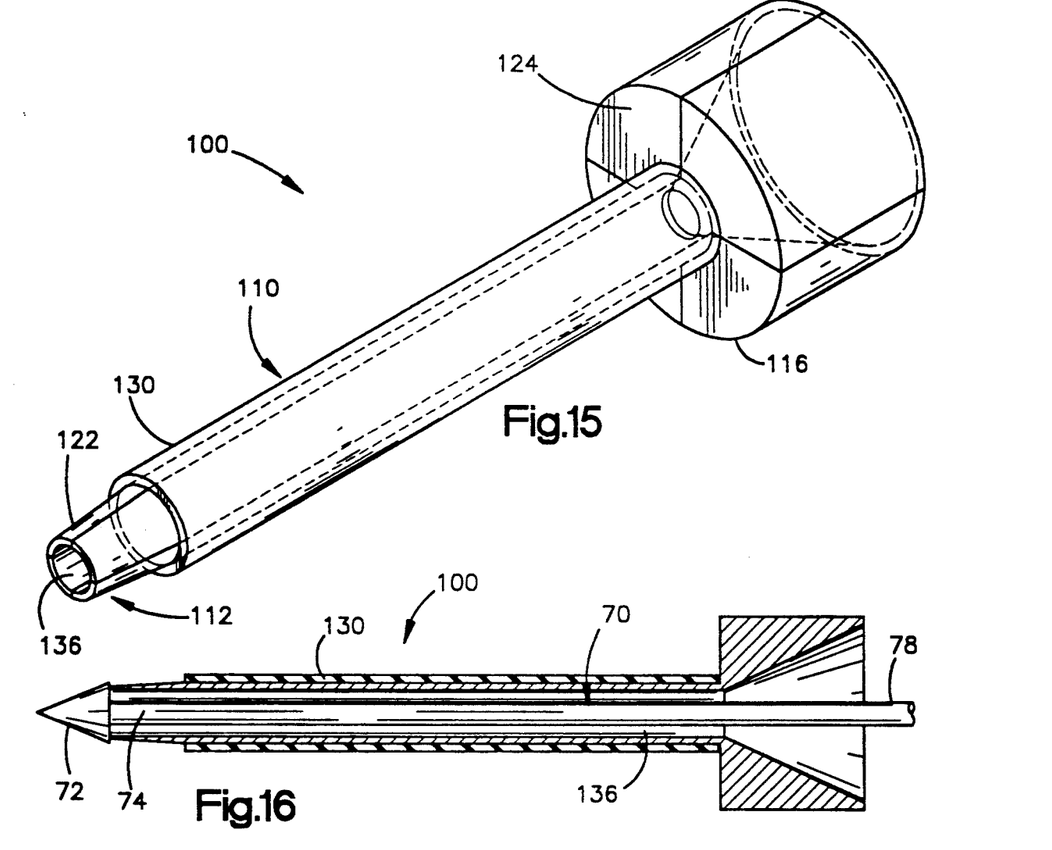
FIG. 15 is a perspective view of the cannula of FIG. 11.
FIG. 16 illustrates the cannula of FIG. 15 with a trocar therein.
Figure 17:
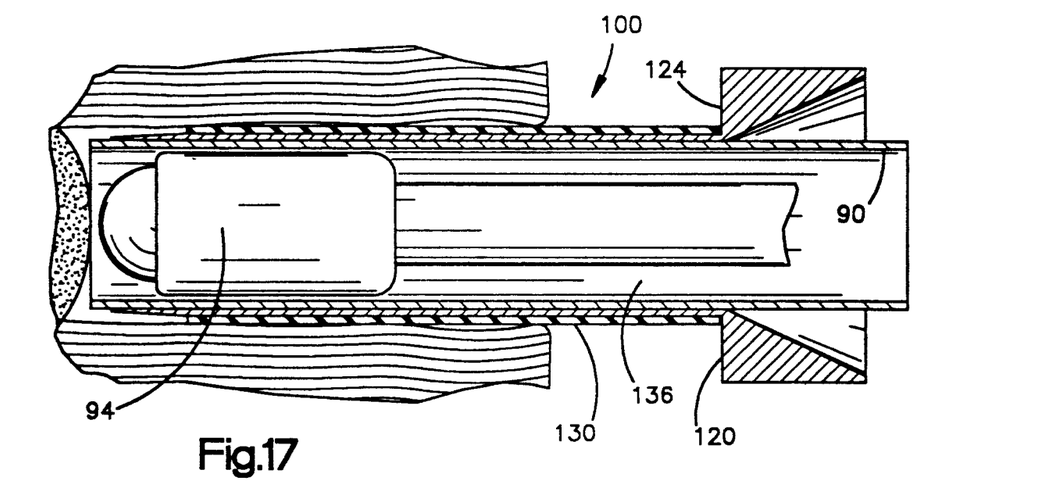
FIG. 17 illustrates the cannula of FIG. 11 in use.

The distal ends 132 of the members 102, 104, 106, and 108 are tapered inwardly for ease of entrance through tissue. The widened proximal end portions 112, 116, 120, and 124 together form a handle for the cannula 100 which also allows entry of an instrument therethrough. The end portions have angled inner surfaces 134 to guide an instrument into the longitudinally extending central instrument passage 1336 of the cannula 100 in the direction indicated by the arrow 138. The handle (proximal end) portion of the cannula 100 can be configured to attach instruments to it, or to have a cap screwed onto the end to close the cannula.

The arcuate segments 110, 114, 118, and 122 are surrounded for most of their length by an overlying elastic sheath 140. The elastic sheath 140 is secured to the segments 110, 114, 118, and 122 at proximal and distal locations 142 and 144, to prevent the sheath's sliding off the segments during insertion and removal of the cannula 100. Rubber cement or cyanoacrylate or a similar adhesive can be used to bond the sheath 140 to the segments. The elastic sheath 140 is preferably made of latex or silicone, or of the C-Flex ® material described above. The sheath 140 is of a diameter such that it is stressed even when the cannula 100 is fully contracted. Thus, the sheath 140 constantly biases the segments radially inwardly toward the center of the cannula 100.

Figure 13:
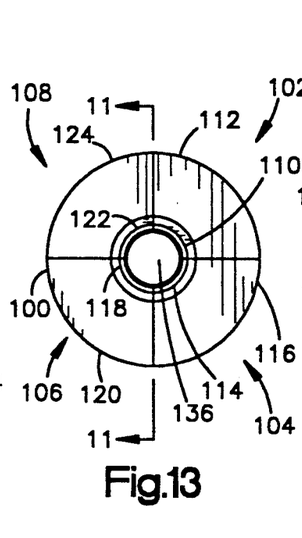
FIG. 13 is a view similar to FIG. 12 with the cannula in a partially expanded condition.
Figure 14:
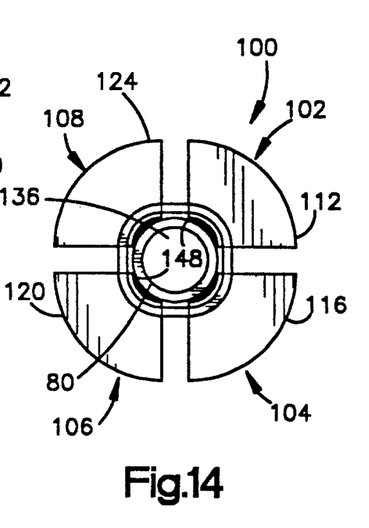
FIG. 14 is a view similar to FIG. 13 with the cannula in a fully expanded condition.

One cannula that has been constructed is 90 mm in length, and about 5 mm in diameter when aligned in a tube form as shown in FIGS. 12-14. The members can collapse (overlap onto themselves as shown in FIG. 11) into a smaller diameter. The cannula can expand to about 12+ mm OD.

In use of the cannula 100, the surgeon makes a small incision in the epidermis. He inserts a narrow trocar such as the trocar 70 (FIG. 16) into the central passage 136 of the cannula 100. The pointed end portion 72 of the trocar 70 will project distally. The shaft portion 74 of the trocar 70 is disposed inside the passage 136. The proximal end portion 78 of the trocar 70 extends proximally from the cannula 100.

A trocar should be used with the cannula 100 only when needed. The distal end portion of the cannula 100 is preferably used alone to push through internal tissue once an epidermal incision has been made.

The trocar/cannula assembly is inserted through the incision in the epidermis to the subcutaneous working location. Then, a tubular insert 80 (FIG. 14) is inserted longitudinally between the cannula 100 and the trocar 70. The insert 80 is preferably a hollow metal tube at least as large in ID as the OD of the trocar pointed end portion 72. The trocar 70 can then be removed from the cannula 100, leaving the cannula and the insert 80 in place in the tissue.

As the insert 80 is inserted in the cannula 100, the outer surface of the insert engages longitudinally extending radially inner edges 148 of the members 102, 104, 106, and 108. Because the insert 80 is larger in diameter than the trocar 70, during insertion of the insert, the cannula 100 is expanded radially outwardly, as seen in a comparison of FIGS. 12 and 13 (which are not necessarily to scale). The four members 102, 104, 106, and 108 move radially outwardly away from each other. The passage 136 is enlarged. The tissue around the cannula 100 is also stretched. The surgeon has thus made a larger passage for instruments, along its entire length, without cutting tissue.

After the tissue is allowed to relax, the surgeon removes the insert 80. The cannula 100 collapses radially inwardly because of the elastic sheath and because of the force of the tissue around it. But the tissue opening does not necessarily collapse completely, because the tissue is viscoelastic.

The surgeon then puts a second insert 90 (FIG. 17) inside the cannula 100. The second insert 90 is a hollow tube larger in diameter than the first insert 80. Again, the cannula 100 expands further radially outwardly, and the tissue stretches. The surgeon continues with larger and larger inserts, until the tissue opening is as large as desired. The cannula may then be in the expanded condition shown in FIG. 17, with the insert 90 within the cannula 100. The cannula 100 can then be removed proximally, leaving the insert in place. The insert then functions as a normal cannula, allowing insertion and removal of surgical instruments and the like such as the probe illustrated schematically at 94.

The cannula 100 expands radially outwardly along substantially its entire length against the bias of the sheath 130. Thus, the cannula 100 can accommodate through its central instrument passage 136 a surgical instrument or the like having a diameter along its entire length which is greater than the diameter of the cannula in the contracted condition. This is not possible with cannulas which expand only along a portion of their length.

It is contemplated that one would use two different size cannulas 100 to obtain a desired range of expansion. A first, smaller size, would extend from an OD of 2.5 mm to an ID of 7 mm, being about 70 mm in length. A second, larger size, would extend from an OD of 6 mm to an ID of 12 mm, being about 150 mm in length.

A third embodiment of the invention is illustrated in FIGS. 18-27. A rigid hollow needle 200 has a tubular wall with an inner circumferential surface and an outer circumferential surface. The needle 200 has a pointed tip 202. Proximal to the tip 202 is a radially extending opening 204 which communicates with a central passage 206 defined by the inner circumferential surface of the needle 200. The passage 206 extends to the proximal end 208 of the needle 200.

Figure 18:
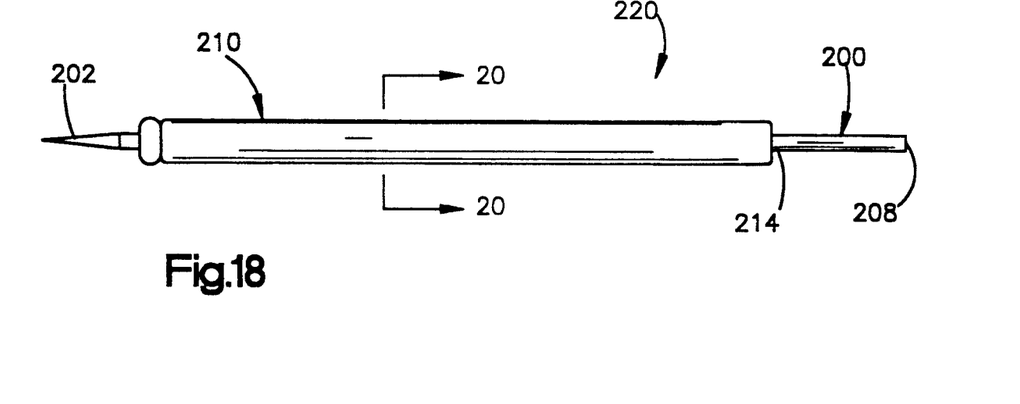
FIG. 18 is a side elevational view of a cannula in accordance with a third embodiment of the present invention, shown in an unexpanded condition.

An elastic balloon 210 is bonded to the needle 200. The balloon 210 is bonded to the needle distally between the tip 200 and a rib 212 adjacent the opening 204. The balloon 210 is also bonded proximally along the needle at 214. The balloon 210 is bonded to the needle 200 so that the balloon 210 does not slide off the needle 210 during insertion and removal. The balloon 210 is preferably made of latex or silicone, or the C-Flex ® material described above. The balloon 210 is of a small enough diameter such that it is stressed even when fully contracted as seen in FIG. 18. The wall thickness of the balloon 210 is exaggerated in the drawings for clarity.

Figure 19:
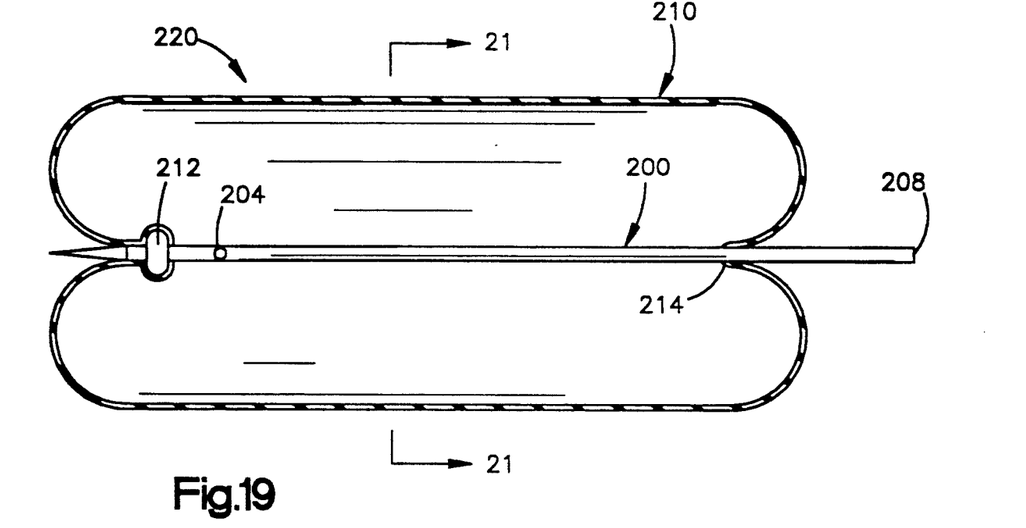
FIG. 19 is a longitudinal sectional view of the cannula of FIG. 18 in a expanded condition.
Figure 20:
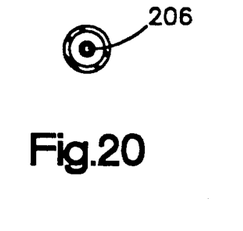
FIG. 20 is a sectional view taken along line 20—20 of FIG. 18.
Figure 21:
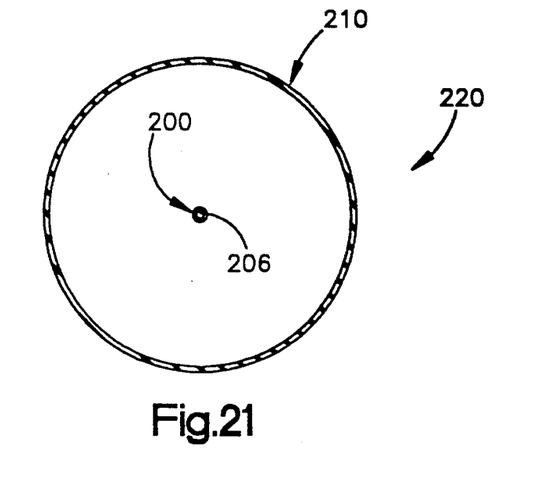
FIG. 21 is a sectional view taken along line 21—21 of FIG. 19.
Figures 22, 23, 24, 25, 26, 27:
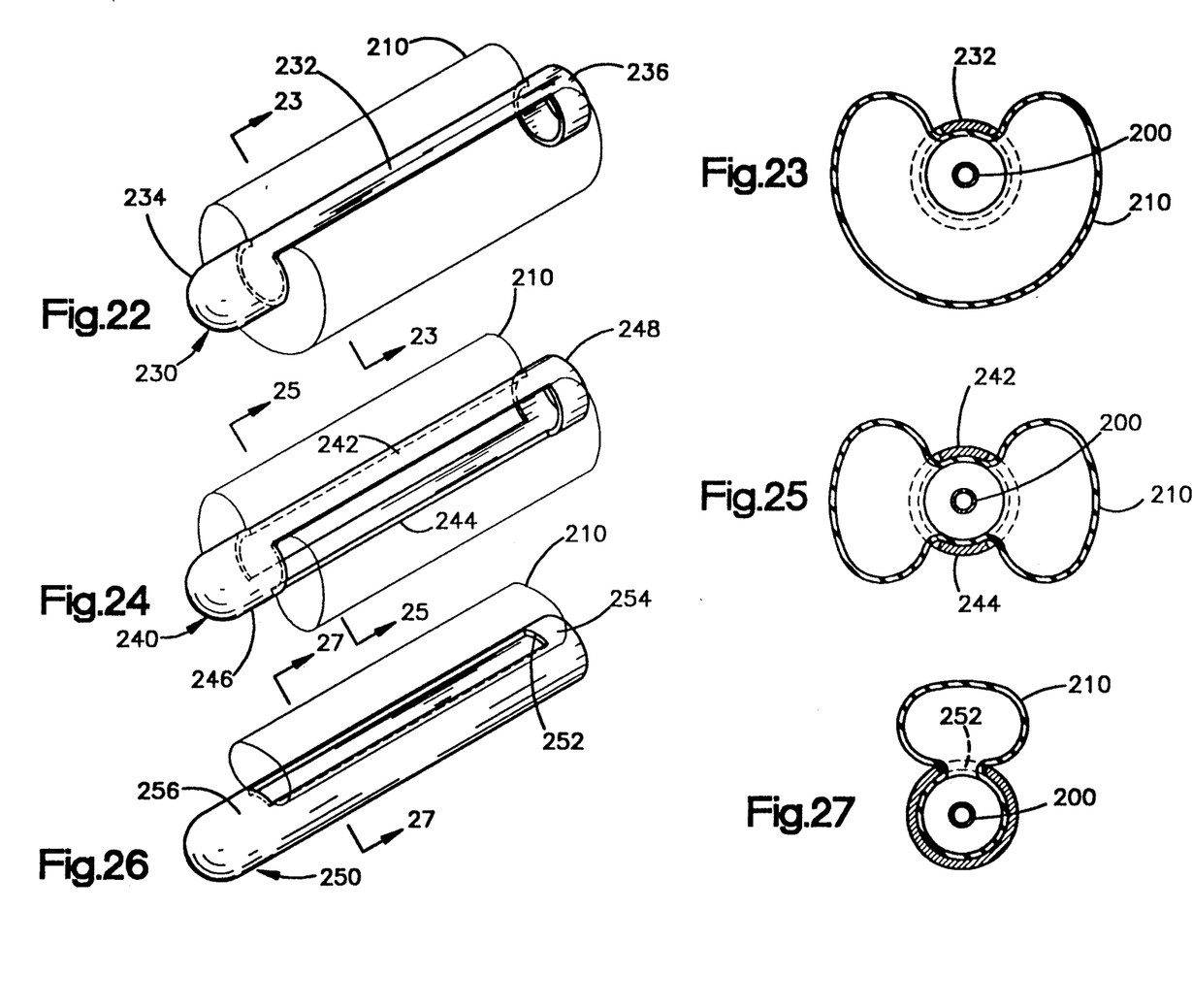
FIG. 22 shows the cannula of FIGS. 18-21 in use with a shape-controlling sleeve.
FIG. 23 is a sectional view taken along line 23—23 of FIG. 22.
FIG. 24 shows the cannula of FIGS. 18-21 in use with a second shape-controlling sleeve.
FIG. 25 is a sectional view taken along line 25—25 of FIG. 24.
FIG. 26 shows the cannula of FIGS. 18-21 in use with a third shape-controlling sleeve.
FIG. 27 is a sectional view taken along line 27—27 of FIG. 26.

Together, the needle 200 and the balloon 210 form an expandable cannula 220. The cannula 220 is inserted in tissue (not shown) to the desired location. Then the balloon 210 is inflated by the introduction of fluid under pressure through the passage 206 and the opening 204 into the interior of the balloon 210. The balloon 210 expands radially outwardly to move tissue.

The cannula 220 can be inserted (unexpanded) into the body as an ordinary needle would be used for drawing blood. The balloon 210 is then inflated to expand the surrounding tissues and create a cavity. The viscoelastic nature of the tissue allows the cavity to be maintained when the balloon 210 is rapidly deflated and the cannula 220 is removed. This cavity can then be used as an initial passage for a more conventional cannula or for an expandable cannula, and thus eliminate the need to make an initial incision. The cannula 220 has therefore without cutting tissue made an opening large enough for the passage of surgical instruments.

Alternatively, an insert (not shown) similar to the inserts 80 and 90 (FIGS. 1-9) can be slid over the expanded cannula 220. The cannula 220 can then be removed and the insert used as an ordinary cannula.

In one cannula 220 embodiment which has been constructed, the needle 200 is an 18 gauge needle, about 0.42" in diameter. The balloon 210 is about 1.25" long. The balloon 210 when unexpanded on the needle 200 is about 0.60" in diameter, and expands to about 0.315" in diameter. With appropriate material selection, there can be obtained 980% expansion (to failure) of the balloon 210.

One of a series of sleeves can be slid proximally over the cannula 220 prior to expansion to control its expansion. A few examples are illustrated in FIGS. 22-27.

A sleeve 230 (FIGS. 22 and 23) has a single arcuate segment 232 extending between circular end portions 234 and 236. The balloon 210 expands into a kidney shape at all areas between the end portions 234 and 236 other than the area covered by the segment 232. A sleeve 240 (FIGS. 24 and 25) has two arcuate segments 242 and 244 extending between circular end portions 246 and 248. The balloon 210 expands outwardly at all areas between the end portions 246 and 248 other than the areas covered by the segments 242 and 244. A sleeve 250 (FIGS. 26 and 27) has a single arcuate slot 252 extending between circular end portions 254 and 256. The balloon 210 expands outwardly only through the slot 252. Thus, it can be seen that the shape of the balloon 210 can be controlled as it expands.

Figures 28, 29, 30:
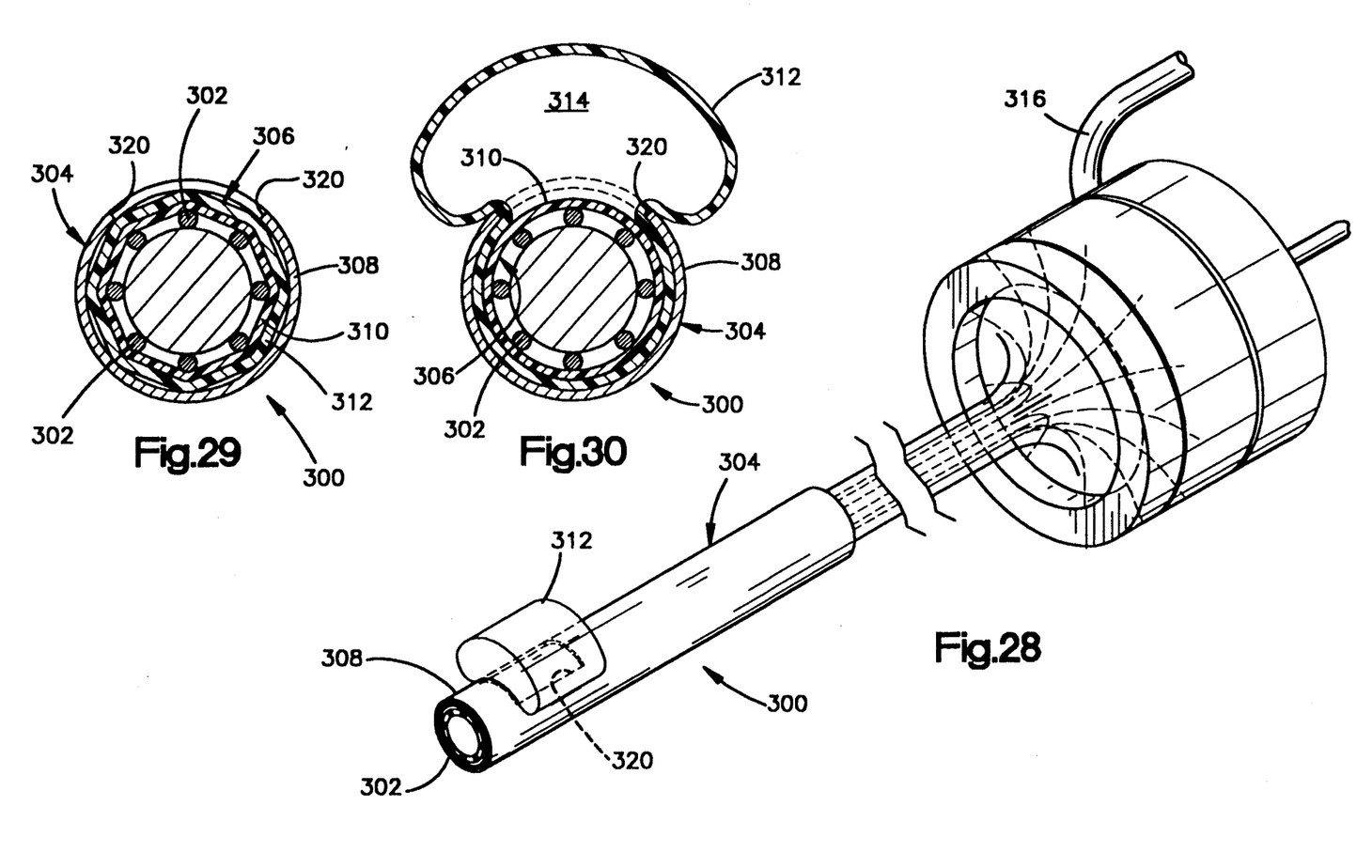
FIG. 28 is a perspective view of a cannula forming another embodiment of the invention.
FIG. 29 is a sectional view of the cannula of FIG. 28, the cannula being shown in a retracted condition.
FIG. 30 is a sectional view of the cannula of FIG. 28, the cannula being shown in an expanded condition.

The expandable cannulas of the present invention may be designed to selectively expand at a location at or near the distal end. This is illustrated in FIGS. 28-30. An expandable cannula 300 similar to the expandable cannula 10 (FIGS. 1-9) includes a plurality of longitudinally extending wires 302. Instead of an elastic sheath like the sheath 18 (FIGS. 1-9), the cannula 300 includes an inflatable sheath 304. The sheath 304 includes an inner sheath member 306 and an outer sheath member 308.

The inner sheath member 306 is of a double-walled construction, including an inner wall 310 and an outer wall 312. An annular inflation volume 314 separates the inner wall 310 and the outer wall 312. Fluid under pressure such as air, saline, etc. may be introduced into the inflation volume 314 through a fluid port 316. The inner sheath member 306 overlies the wires 302.

When fluid under pressure is introduced into the inflation volume 314 through the fluid port 316, the inner sheath member 306, including both the inner wall 310 and the outer wall 312, expands radially outwardly. Radially outward expansion of the inner sheath member 306 is limited by the outer sheath member 308. The outer sheath member 308 is a single-layer sheath overlying the inner sheath member 306. A notch 320 is cut out of the outer sheath member 308. The inner sheath member 306 can expand radially outwardly only at the location of the notch 320 in the outer sheath member 308.

The notch 320, or any similar opening in the outer sheath member 308, may be placed at or near the distal end of the cannula 300. This will stabilize the cannula 300 in the tissue, at the closest possible location to the work area off the distal end of the cannula.

From the above description of the invention, those skilled in the art will perceive improvements, changes and modifications in the invention. Such improvements, changes and modifications within the skill of the art are intended to be covered by the appended claims.

We claim:

1. An expandable cannula having a contracted condition and being expandable radially outwardly along substantially its entire length from the contracted condition to an expanded condition, said expandable cannula comprising:

a plurality of longitudinally extending wires extending generally parallel to each other in a generally circular array when said expandable cannula is in the expanded condition, said wires defining between them a central instrument passage in said cannula for receiving surgical instruments and the like therethrough, said longitudinally extending wires have proximal ends disposed at a proximal end of said cannula and distal ends disposed a distal end of said cannula, said cannula including securing means disposed at said proximal end of said cannula, said securing means connected with said proximal ends of said wires and connecting together respective proximal ends of said wires to block separation of said wires, said securing means having a diameter approximately equal to said second, larger diameter of said expandable cannula; and an elastic sheath overlying said wires, said elastic sheath biasing said cannula into the contracted condition;

said elastic sheath comprises a tubular elastic member disposed circumferentially around said plurality of longitudinally extending wires, said tubular elastic member extending longitudinally along said wires for a major portion of the length of said wires, said tubular elastic member elastically stretching radially outwardly from a first, smaller diameter to a second, larger diameter when said cannula is expanded from the contracted condition to the expanded condition;

said cannula being expandable radially outwardly along substantially its entire length against the bias of said sheath from the contracted condition to the expanded condition upon insertion of a dilator member into said central instrument passage, to accommodate through the central instrument passage a surgical instrument or the like having a diameter along its entire length which is greater than the diameter of said cannula in the contracted condition.

2. An expandable cannula as set forth in claim 1 wherein said securing means comprises coaxially aligned first and second clamping rings having aligned central passages therethrough, said first and second clamping rings being secured together with said proximal ends of said longitudinally extending wires clamped between said first and second clamping rings.

3. An expandable cannula as set forth in claim 2 wherein said elastic sheath has a proximal end clamped between said first and second clamping rings to block disengagement of said sheath from said longitudinally extending wires during insertion and removal of said expandable cannula.

4. An expandable cannula as set forth in claim 1 wherein said securing means has a threaded portion for receiving thereon a luer lock.

5. An expandable cannula having a contracted condition and being expandable radially outwardly along substantially its entire length from the contracted condition to an expanded condition, said expandable cannula comprising:
 a plurality of longitudinally extending wires extending generally parallel to each other in a generally circular array when said expandable cannula is in the expanded condition, said wires defining between them a central instrument passage in said cannula for receiving surgical instruments and the like therethrough; and
 an elastic sheath overlying said wires, said elastic sheath biasing said cannula into the contracted condition;
 said cannula being expandable radially outwardly along substantially its entire length against the bias of said sheath from the contracted condition to the expanded condition upon insertion of a dilator member into said central instrument passage, to accommodate through the central instrument passage a surgical instrument or the like having a diameter along its entire length which is greater than the diameter of said cannula in the contracted condition;
 said wires have outer surface portions disposed radially inwardly in said cannula and forming contact surfaces for surgical instruments and the like inserted through the central instrument passage of said cannula, said sheath having an outer circumferential surface engaging tissue when said cannula is in use, said wires blocking engagement with said elastic sheath of instruments inserted through the central instrument passage of said cannula, said sheath blocking engagement of tissue with said wires, and said sheath and said wires blocking engagement of tissue with any instruments inserted through said cannula.

6. An expandable cannula as set forth in claim 5 wherein said sheath is bonded to said wires at at least one location axially along the length of said cannula.

7. An expandable cannula as set forth in claim 5 wherein said wires are made from metal and said sheath is made from a material selected from the group consisting of plastic and latex.

8. An expandable cannula as set forth in claim 5 wherein said wires are metal wires about 0.015" in diameter and said sheath is made from a material selected from the group consisting of latex, silicone, C-Flex ®, and similar elastic materials.

9. An expandable cannula as set forth in claim 5 which is expandable from about 2 mm to about 6 mm or more.

10. An expandable cannula as set forth in claim 5 wherein said wires have linear longitudinal central axes along substantially the entire length of said cannula.

11. An expandable cannula as set forth in claim 5 wherein said elastic sheath comprises a tubular elastic member disposed circumferentially around said plurality of longitudinally extending wires, said tubular elastic member extending longitudinally along said wires for a major portion of the length of said wires, said tubular elastic member elastically stretching radially outwardly from a first, smaller diameter to a second, larger diameter when said cannula is expanded from the contracted condition to the expanded condition.

12. An expandable cannula having a contracted condition and being expandable from the contracted condition to an expanded condition, said expandable cannula comprising a tube having a longitudinally extending central passage for receiving surgical instruments and the like, said tube being expandable under the influence of force applied against the inside of said tube to increase the cross sectional area of the central passage through said tube upon expansion of said cannula from the contracted condition to an expanded condition, and a plurality of wires enclosed by said tube and having longitudinal central axes extending parallel to the longitudinal central axis of said tube throughout at least substantially the entire length of said wires, said wires having a length which is at least substantially as great as the length of said tube, said wires being disposed in an array having a first cross sectional area when said cannula is in the contracted condition, said wires being disposed in an array having a second cross sectional area when said cannula is in the expanded condition, said second cross sectional area being greater than said first cross sectional area.

13. An expandable cannula as set forth in claim 12 wherein said wires have longitudinally extending side surface areas which are pressed against longitudinally extending inner side surface areas of said tube under the influence of force applied against said wires to effect expansion of said cannula from the contracted condition to the expanded condition.

14. An expandable cannula as set forth in claim 12 wherein said wires have longitudinally extending side surface areas forming contact surfaces for a member inserted into the central passage in said tube, said tube having an outer side surface engaging tissue when said cannula is in use, each of said wires blocking engagement of a longitudinally extending portion of said tube with the member inserted into the central passage in said tube, said tube blocking engagement of tissue with at least the portion of said wires and with at least the portion of the member disposed in said tube.

15. A cannula as set forth in claim 12 wherein said wires are disposed in engagement with an inner side surface of said tube, said tube being elastically expandable outward along substantially its entire length against the bias of the natural resiliency of said tube upon insertion of a dilator member into the central passage in said tube, to accommodate through the central passage a surgical instrument or the like having a cross sectional area which is greater than a cross sectional area of said central passage when said cannula is in the retracted condition.

16. An expandable cannula, said cannula comprising an expandable tube having an inner side surface which at least partially defines a passage which receives a surgical instrument or the like, insert means insertable into the passage in said tube to effect expansion of said tube and to increase the cross sectional area of the passage from a first cross sectional area to a second cross sectional area, and a plurality of longitudinally extending wires disposed along the inner side surface of said tube, each of said wires having longitudinally extending surface means which is engaged by said insert means to enable each of said wires to transmit force from said insert means to said tube.

17. An expandable cannula as set forth in claim 16 wherein said surface means on each of said wires is engaged by said insert means at a location spaced from the inner side surface of said tube.

18. An expandable cannula as set forth in claim 16 and wherein said wires have longitudinal axes which extend parallel to the longitudinal central axis of said tube throughout at least substantially the entire length of said wires, said wires having a length which is at least substantially as great as the length of said tube.

19. An expandable cannula as set forth in claim 16 wherein said surface means on each of said wires includes a longitudinally extending surface area which is pressed against the inner side surface of said tube under the influence of force transmitted from said insert means to effect expansion of said tube.

20. An expandable cannula as set forth in claim 16 wherein said tube has an outer side surface which engages tissue when said cannula is in use, each of said wires blocking engagement of a longitudinally extending portion of the inner side surface of said tube with said insert means when said insert means is inserted into the passage in said tube, said tube blocking engagement of tissue with at least a portion of said wires and with at least a portion of said insert means when said insert means is inserted into said tube and said cannula is in use.

21. An expandable cannula as set forth in claim 16 wherein said insert means has a cylindrical outer side surface, each of said wires being engageable with said outer side surface of insert means to maintain a longitudinally extending portion of the inner side surface of said tube spaced from the outer side surface of said insert means.

22. An expandable cannula as set forth in claim 16 wherein said tube continuously presses said wires inwardly against an outer side surface of said insert means when said insert means is inserted in the passage in said tube.

23. An expandable cannula as set forth in claim 16 further including connector means for interconnecting ends of said wires and holding said ends of said wires against movement relative to each other, said connector means holding said ends of said wires in a circular array which has an area which is at least as great as the second cross sectional area of the passage in said tube.

24. An expandable cannula as set forth in claim 16 wherein each of said wires extends between opposite end portions of said tube and has a longitudinal central axis which is parallel to a longitudinal central axis of said tube.

25. A method comprising the steps of inserting a cannula into a patient's body, and expanding the cannula to increase the cross sectional area of a passage extending through the cannula from a first cross sectional area to a second cross sectional area, said step of expanding the cannula including sliding an insert along side surfaces of a plurality of wires which are disposed in the cannula and extend between opposite end portions of the cannula.

26. A method as set forth in claim 25 wherein said step of expanding the cannula includes transmitting force from the wires to a tube to expand the tube as the insert is slid along side surfaces of the wires.

27. A method as set forth in claim 26 wherein said step of expanding the cannula includes the step of maintaining the insert in a spaced apart relationship with the tube while sliding the insert along side surfaces of the wires.

28. A method as set forth in claim 25 wherein said step of expanding the cannula includes increasing the cross sectional area of the passage from the second cross sectional area to a third cross sectional area, said step of increasing the cross sectional area of the passage from the second cross sectional area to a third cross sectional area including sliding a second insert having a cross sectional area which is greater than the second cross sectional area along the side surfaces of the plurality of wires in the cannula.

29. A method as set forth in claim 25 wherein said step of sliding an insert along side surfaces of a plurality of wires includes moving the insert along a path having a longitudinal axis which is parallel to longitudinal axes of the wires.

30. A method comprising the steps of inserting a trocar into a passage in a cannula, thereafter, inserting an end portion of the trocar and an end portion of the cannula into a patient's body with the end portion of the trocar extending beyond the end portion of the cannula, thereafter, expanding the cannula to increase the cross sectional area of the passage in the cannula, said step of expanding the cannula including inserting a tubular member into the passage in the cannula with the tubular member disposed between the trocar and the cannula, and withdrawing the trocar from the patient's body and the cannula by moving the trocar through a passage in the tubular member wherein said step of inserting the tubular member into the passage in the cannula includes sliding the tubular member along side surfaces of a plurality of wires which are disposed in the cannula.

31. A method as set forth in claim 30 wherein said step of inserting the trocar into the passage in the cannula includes sliding the trocar along side surfaces of a plurality of wires which are disposed in the cannula, said step of inserting the tubular member into the passage in the cannula includes sliding the tubular member along side surfaces of the plurality of wires and moving the plurality of wires out of engagement with the trocar.

32. A method comprising the steps of inserting a cannula into a patient's body, expanding the cannula to increase the cross sectional area of a passage in the cannula from a first cross sectional area to a second cross sectional area, said step of expanding the cannula including inserting a first longitudinally extending member having a cross sectional area which is greater than the first cross sectional area into the passage in the cannula, and, thereafter, further expanding the cannula to increase the cross sectional area of the passage in the cannula from the second cross sectional area to a third cross sectional area, said step of further expanding the cannula including inserting a second longitudinally extending member having a cross sectional area which is greater than the second cross sectional area into the passage in the cannula, wherein said step of inserting a first longitudinally extending member into the passage in the cannula includes sliding the first member along said surfaces of a plurality of wires which are disposed in the cannula, said step of inserting the second member into the cannula includes sliding the second member along the surfaces of the plurality of wires and moving the plurality of wires out of engagement with the first member.

33. A method as set forth in claim 32 wherein the second longitudinally extending member is a tubular member and said step of inserting the second member into the cannula is performed with the first member in the cannula, said method further including withdrawing the first member from cannula by moving the first member through a passage in the tubular second member after having performed said step of inserting the second member into the passage in the cannula.

34. A method as set forth in claim 32 wherein said steps of inserting a first member into the passage in the cannula and inserting a second member into the passage in the cannula includes sliding at least one of said members along the side surfaces of wires which are disposed in the cannula.

35. A method as set forth in claim 32 wherein the cannula includes a tube and a plurality of longitudinally extending wires disposed along an inner side of the tube, said step of inserting the first member into the passage in the cannula including engaging the wires with the first member and expanding the tube under the influence of force transmitted from the first member through the wires to the tube.

36. A method as set forth in claim 35 wherein said step of inserting the second member into the passage in the cannula includes engaging the wires with the second member and expanding the tube under the influence of force transmitted through the wires to the tube.

37. A method as set forth in claim 36 wherein said step of inserting the second member into the passage in the cannula is performed with the first member in the passage in the cannula.

38. A method comprising inserting a cannula having a plurality of spaced apart, non-intersecting longitudinally extending wires enclosed by a tube into a patient's body, thereafter, inserting a member into the tube, and utilizing the wires to hold longitudinally extending portions of an inner side surface of the tube spaced apart from an outer side surface of the member during insertion of the member into the tube.

39. A method as set forth in claim 38 further including the step of pressing the wires against the outer side surface of the member with the tube.

40. A method as set forth in claim 38 wherein said step of inserting the member into the tube includes expanding the tube under the influence of force transmitting from the outer side surface of the member through the wires to the tube.

41. A method as set forth in claim 38 wherein the wires are disposed in the tube in an array having a first cross sectional area prior to insertion of the member into the tube, said step of inserting the member into the tube includes increasing the cross sectional area of the array of wires from the first cross sectional area to a second cross sectional area which is greater than the first cross sectional area.

42. A method as set forth in claim 38 wherein said step of inserting a member into the tube includes sliding the member along side surfaces of the wires in the tube.

43. A method as set forth in claim 38 further including the step of inserting a second member into the tube while the first member is disposed in the tube to expand the tube.

44. A method as set forth in claim 38 further including the step of telescoping a tubular second member around the first member while the first member is disposed in the tube, said step of telescoping a second member around the first member including utilizing the wires to hold longitudinally extending portions of the inner surface of the tube spaced apart from an outer side surface of the second member.

45. A method as set forth in claim 44 further including the step of withdrawing the first member from the tube after performing said step of telescoping a second member around the first member.

46. A method as set forth in claim 44 wherein said step of telescoping a second member around the first member includes moving the wires out of engagement with the outer side surface of the first member.

* * * * *